United States Patent [19]
Delgrosso

[11] 4,206,353
[45] Jun. 3, 1980

[54] ANALYZING SYSTEM

[75] Inventor: Raymond Delgrosso, Yonkers, N.Y.

[73] Assignee: Technicon Instruments Corporation, Tarrytown, N.Y.

[21] Appl. No.: 910,727

[22] Filed: May 30, 1978

[51] Int. Cl.² ............................................. G01N 21/34
[52] U.S. Cl. .................................. 250/343; 250/338; 23/232 R
[58] Field of Search .............. 250/338, 343; 23/232 R

[56] References Cited

U.S. PATENT DOCUMENTS

| | | | |
|---|---|---|---|
| 3,407,124 | 10/1968 | Pasik | 23/232 R X |
| 3,836,255 | 9/1974 | Schuman | 250/343 X |
| 3,963,927 | 6/1976 | Bruce et al. | 250/338 |

OTHER PUBLICATIONS

M. W. Street, Jr., et al, "Hidden–Insect Detection by Infrared Carbon Dioxide Gas Analysis", U.S. Dept. of Agriculture Rpt. (ARS-S-85) pp. 1–10 (Mar. 1976).

Primary Examiner—Joseph Scovronek
Attorney, Agent, or Firm—S. P. Tedesco

[57] ABSTRACT

A system for detecting live insects in a commodity sample features forming a closed-loop between a stored quantity of fluid and a sample cell and a reference cell. The closed-loop and the stored fluid ensure a controlled environment during incubation and analysis of the commodity sample. This controlled environment achieves a greater sensitivity and reproducibility than prior systems.

14 Claims, 6 Drawing Figures

| FLOW THRU | VALVE STATUS |
|---|---|
| CHAMBER I | V1, V2, V3, V4 DEENERGIZED |
| CHAMBER II | V1, V3 DEENERGIZED V2, V4 ENERGIZED |
| CHAMBER III | V1, V3 ENERGIZED V2, V4 DEENERGIZED |

FIG. 1
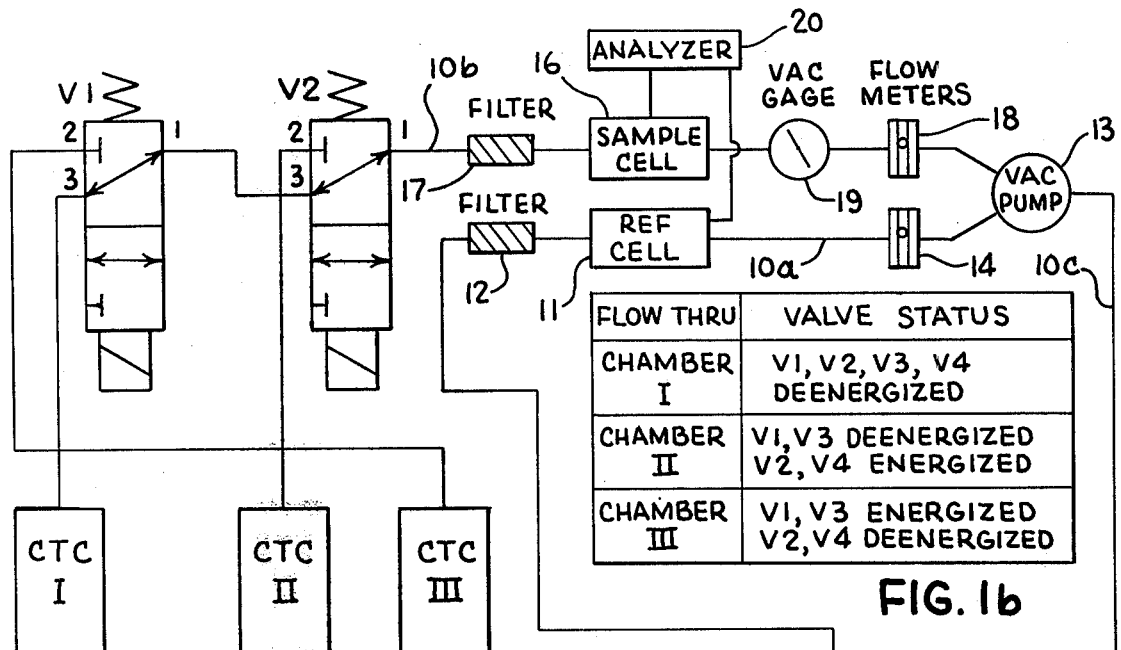
FIG. 1b
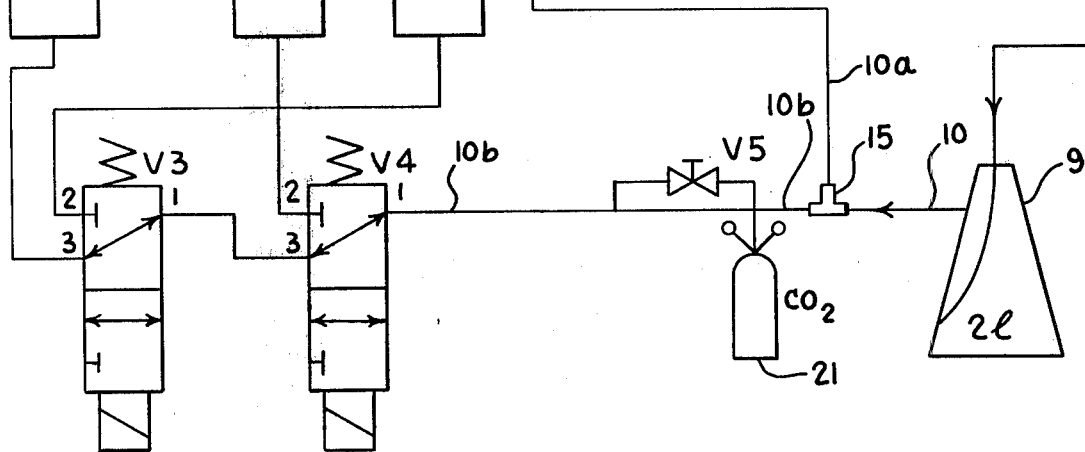
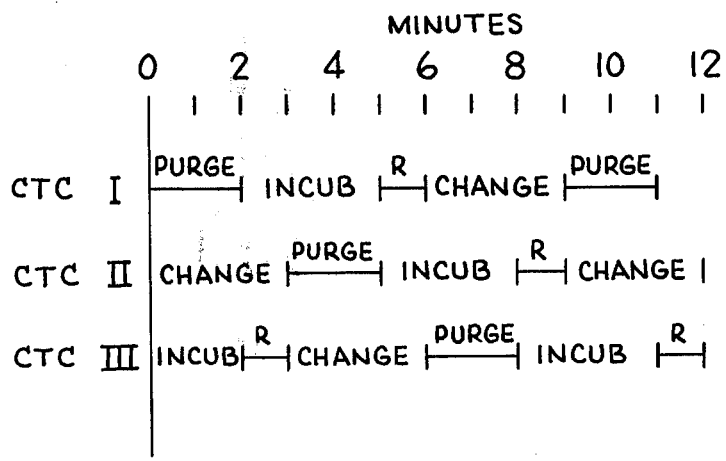
FIG. 1a

FIG. 2
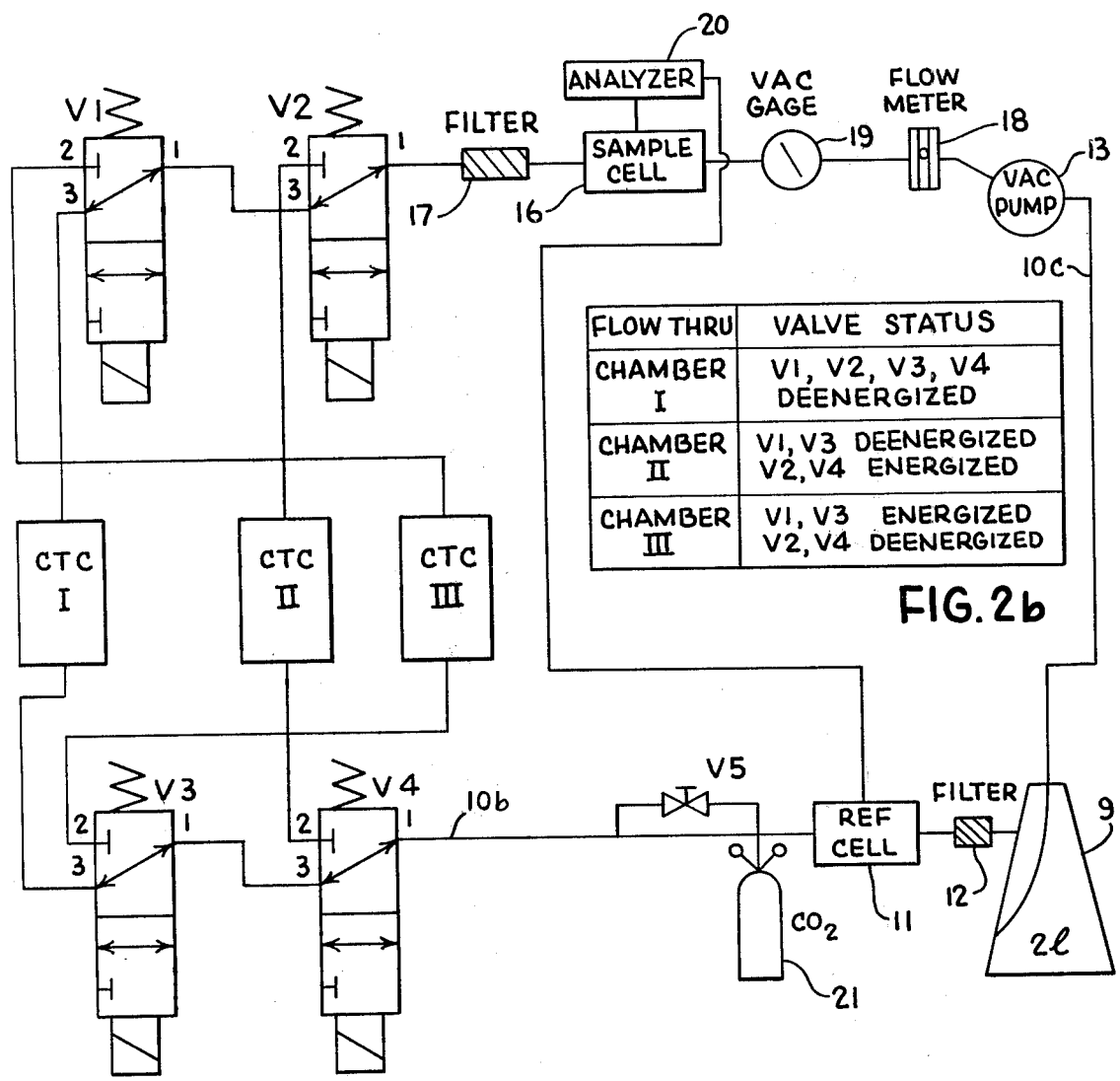
FIG. 2b
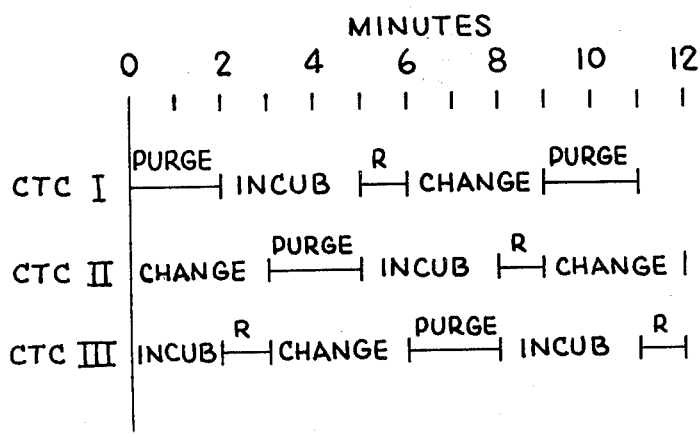
FIG. 2a

ANALYZING SYSTEM

FIELD OF THE INVENTION

This invention relates to method and analysis of materials, and more particularly, to a method and system for analyzing a commodity sample for the presence of carbon dioxide as an indication of live insect infestation.

BACKGROUND OF THE INVENTION

Recently, a carbon dioxide analyzing system has been developed for detecting live insects in commodity samples. A commodity sample is introduced into a commodity test chamber (CTC), and the system is closed to the environment for a given period of time. During this incubation time, any insects in the sample will respire or otherwise give off carbon dioxide. After this given period of time, the system is opened to the ambient air, and the carbon dioxide in the test chamber is forced under pressure or vacuum to a sample cell. The carbon dioxide level in this sample cell is then compared with a reference level carbon dioxide in a reference cell. Infestation will be indicated in the commodity sample, when the two levels do not coincide.

The above system is described in the literature in the following articles: "Detection of Hidden Insects" by William A. Bruce and Marion W. Street, Jr., Department of Agriculture, Washington, D.C., 18 June, 1975, (PB 248 002); Department of Agriculture Report (ARS-S-85) by William A. Bruce and Marion W. Street, Jr., March, 1976; and "CO$_2$ Analyzer Detects Insects Hidden in Foods" by William A. Bruce and Marion W. Street, Jr., Food Engineering, February, 1976.

Reference is additionally made to U.S. Pat. No. 3,963,927, issued June 15, 1976.

While this prior system has made a major contribution in the art of insect detection, certain shortcomings have been noted to exist. This system has been found to give results which are sometimes neither accurate nor reproducible, as the system is open to the ambient surroundings during the transfer of the carbon dioxide from the commodity test chamber (CTC) to the sample cell. The ambient air is sucked into the system as the carbon dioxide in the test chamber is pumped to the sample cell. The ambient air will normally contain the same level of carbon dioxide as in the reference cell, which was open to ambient air prior to incubation. If such is the case, the system will give accurate results. However, this is not always true. Ambient conditions may change during incubation, as particularly so when people breathe or smoke near the system inlet, so as to cause a higher carbon dioxide concentration to exist in the air sucked into the sample cell. Thus, false readings often result.

The reliability of the system is dramatically impaired by these extraneous concentrations of carbon dioxide, particularly since very low levels of carbon dioxide are to be measured against a high reference level. Thus, a person breathing near the system can generate enough carbon dioxide to give an indication of infestation, when in actuality no insects are present in the sample.

A single insect may generate only several parts per million (ppm) of carbon dioxide in a few minutes. This minute amount of carbon dioxide must be measured against an ambient background of approximately 270-300 ppm. Thus, even the slightest change in ambient surroundings of the system will greatly influence the accuracy and reliability of the analysis.

The present invention seeks to overcome the above drawbacks of the prior art by providing a controlled background level of carbon dioxide in both the sample and reference cells. This controlled environment ensures that any change in the level of carbon dioxide in the sample cell is due entirely to infestation, and not to any changes in the ambient surroundings. The invention contemplates providing a closed-loop system to avoid extraneous carbon dioxide from entering the system and, furthermore, supplying each of the sample and reference cells with a controlled amount of background carbon dioxide, whereby the reference, or background, level of carbon dioxide remains constant throughout the analysis.

It is known to have closed loops in other types of analyzing systems, such as described in "A Rapid and Specific Method for the Estimation of Glucose Using an Oxygen Electrode and Simple Differentiating Circuit" by H. L. J. Makin, P. J. Warren and J. D. Edridge, Clinica Chimica Acta, 84 (1978), pages 137–143. However, such prior systems have used the closed loop as a means to save the enzyme for reuse, and not to precisely control the system parameters during the analysis process.

SUMMARY OF THE INVENTION

The present invention contemplates positive control of the environment during actual tests by effecting the analysis in closed-loop system, whereby the background level of the condition to be measured, e.g., the presence of carbon dioxide, is precisely controlled. A container including, for example, ambient air is included in the closed-loop system in fluid flow communication with the commodity test chamber, so as to maintain a constant level of background carbon dioxide during the incubation and analysis phases, as hereinafter described. A reference cells is included within the closed-loop system, the reference cell providing a constant carbon dioxide level against which measurement of any increased concentration of carbon dioxide in the commodity test chamber is measured.

The sample in the commodity test chamber (CTC) is allowed to incubate, i.e., any insects are given time to respire in order to generate carbon dioxide. Subsequent to the incubation phase, the ambient air in the commodity test cell, along with any carbon dioxide which is generated, is transferred to the sample cell by air from the container; air from the same container is concurrently transferred to the reference cell. If insects are present in the sample, the carbon dioxide level will be higher in the sample cell than in the reference cell. This difference is detected by an analyzer, which is generally an infrared detection device.

It is an object of this invention to provide an improved method and system for analysis of materials, whereby system parameters are precisely controlled, and are independent of the ambient conditions surrounding the system, during the analysis process, so as to ensure precise and reproducible results.

It is an object of this invention to provide an improved method and system for detecting infestation by live insects in a commodity sample.

It is another object of the invention to provide a system for detecting infestation by live insects in a commodity sample which features a controlled internal environment.

It is a further object of this invention to provide a system for detecting infestation by live insects in a commodity sample, which system is more accurate and reliable than prior such systems.

DESCRIPTION OF THE DRAWINGS

These and other objects of the invention will become more apparent and will be better understood with reference to the following detailed description taken in conjunction with the accompanying drawings, in which:

FIG. 1 shows a schematic pneumatic diagram of the system of the invention, with the sample and reference cells arranged in parallel;

FIG. 1a depicts a typical timing diagram for operating the system of FIG. 1;

FIG. 1b illustrates the valving sequence for the system of FIG. 1;

FIG. 2 shows an alternate schematic diagram for the system diagram for the system of FIG. 1, with the sample and reference cells arranged in series;

FIG. 2a depicts a typical timing diagram for operating the system of FIG. 2; and FIG. 2b illustrates the valving sequence for the system of FIG. 2.

DETAILED DESCRIPTION

Generally speaking, the invention is for a method and system for detecting the infestation of live insects within a commodity sample. A given quantity of fluid is stored. Generally, this fluid is air having a certain content of carbon dioxide. A portion of the stored fluid is circulated through a reference cell of the system in a controlled manner to establish a controlled level of carbon dioxide. The commodity sample is deposited in a commodity test chamber to allow the sample to incubate, or otherwise generate carbon dioxide. A portion of the stored fluid is circulated through the commodity test chamber in a controlled manner in order to transfer any of the generated carbon dioxide from the commodity chamber to a sample cell. The sample cell and the reference cell are analyzed for a difference in carbon dioxide level. The presence of living insects in the commodity sample will be detected by a difference in carbon dioxide level between the sample cell and the reference cell.

Now referring to FIG. 1, a pneumatic circuit diagram is shown which illustrates the present invention. The system comprises a container 9, filled with ambient air. A conduit 10 extends from container 9 and divides into two conduit paths 10a and 10b via junction 15. Conduit 10a is connected to a reference cell 11 via a filter 12. A portion of the air in container 9 is circulated through conduit 10a by means of vacuum pump 13. A flow meter 14 connected in conduit 10a controls the rate of flow through the reference cell 11. Conduit 10b carries a portion of the air in container 9 to a first valve V4. Depending upon the position of valve V4, the air will be directed to either valve V3 or to a second one of three commodity test chambers (CTC), further designated with Roman numerals I, II and III, respectively. Valve V3 also has two positions, whereby the air may be directed to commodity chambers I or III, respectively.

Two valves V1 and V2 are on the downstream side of the commodity test chambers CTC I and CTC III and of commodity test chamber CTC II, respectively, and direct the circulating air from conduit 10b to a sample cell 16 via a filter 17. Filters 12 and 17 trap dust and extraneous matter from entering the cells 11 and 16, respectively. The pump 13 circulates air in conduit 10b as well as conduit 10a. A flow meter 18 in conduit 10b regulates the flow rate through the sample cell 16. A vacuum gauge 19 is in the conduit 10b to gauge the pressure in the system. Air from both conduits 10a and 10b flow at the same rate in order to establish an equal background level of carbon dioxide in each cell 11 and 16, respectively. The air from conduits 10a and 10b is returned to the sealed container 9 via conduit 10c. An analyzer 20 is provided to measure the difference in the carbon dioxide level difference in sample cell 16 and reference cell 11.

A container of carbon dioxide 21 is connected to a dosing valve V5, to introduce a given quantity or charge of carbon dioxide into conduit 10b. This charge is subsequently introduced into sample cell 16 via the valves V1, V2, V3 and V4, so as to calibrate the system.

FIG. 2 is a pneumatic diagram for an alternate circuit arrangement for the invention. The sample cell 16 and reference cell 11 are now arranged in series with respect to container 9 instead of in parallel (FIG. 1). The system of FIG. 2, however, operates in the exact fashion as the system in FIG. 1. Like components have been given the same designations in FIG. 2 as they had in FIG. 1. Because the system is a series flow circuit, only one metering valve 18 is required to regulate the flow through the sample and reference cells.

OPERATION OF THE INVENTION

The operation of the systems shown in FIGS. 1 and 2, will be described with reference to FIGS. 1a, 1b, 2a and 2b. While these diagrams show how three commodity test chambers CTC I, CTC II, and CTC III may be operated in a phased sequence, it should be appreciated that only one commodity test chamber may be used in the system consistent with the invention.

The commodity test chambers CTC I, CTC II, and CTC III are initially filled with grain or another similar type commodity to be tested for infestation by live insects. These chambers are initially open at each end, and are sealed from the ambient surroundings when they are connected into the system. When so connected, they form part of a closed loop defined by conduits 10b and 10c.

In the operation described in FIGS. 1a and 1b, the three filled commodity test chambers CTC I, CTC II, and CTC III are connected into the system and subsequently analyzed in a phased sequence. A typical cycle for each commodity test chamber includes an initial purging or flushing of the chamber with air from container 9. During the purging of commodity test chamber CTC I, for example, the valves V1, V2, V3, and V4 are all deenergized to provide a fluid flow connection between commodity test chamber CTC I and the system to complete the closed loop. At the same time, the other commodity test chambers CTC II and CTC III are not fluidically connected into the system. Rather, as illustrated in FIG. 1a, sample is being changed in commodity test chamber CTC II and commodity test chamber CTC III is in the incubation phase.

The purging of commodity test chamber CTC I accomplishes two purposes: (a) it equilibrates the system by mixing any entrapped air and carbon dioxide in the test chamber with the air in the rest of the closed loop, and (b) the sample in the commodity test chamber is washed clean of any residual carbon dioxide, so that the subsequent measurement of carbon dioxide in the commodity test chamber CTC I will be entirely in respect of live insect respiration.

After the commodity test chamber CTC I has been purged, valves V2 and V4 are energized, thus isolating commodity test chamber CTC I from the rest of the system. During this time, commodity test chamber CTC II is fluidically introduced into the closed loop and purged by the continuously circulating air, via pump 13 (see valve sequence diagram FIG. 1b). It will be seen from FIG. 1b that the commodity test chamber CTC I is now in its incubation phase. The incubation phase of commodity test chamber CTC I allows for the generation of carbon dioxide by live insects over a time period. FIG. 1a shows a three minute incubation time, but naturally, all the times of these cycles can be rearranged to suit the user of the system.

After the incubation phase of commodity test chamber CTC I, valves V1 and V3 are energized to allow air to flow through such chamber. This is the one minute analysis time designated R in FIG. 1a. The air flowing through commodity test chamber CTC I at this time will sweep the contents, including any generated carbon dioxide, from such chamber to sample cell 16 for analysis. It will be noted that at this time commodity test chamber CTC II is starting its three minute incubation phase, and is closed to the system (see FIG. 1b).

If carbon dioxide has been generated by live insects in commodity test chamber CTC I, then the analyzer 20 will detect a difference between carbon dioxide levels in the reference cell 11 and the sample cell 16.

After the analysis, the sample in commodity test chamber CTC I can be changed, as shown in FIG. 1a, by removing such chamber from the system.

The cycle for commodity test chamber CTC I can now be repeated for a new sample with the subsequent reintroduction of such chamber into the system.

It will be seen by observing FIGS. 1a and 1b, that the testing of all three commodity test chambers, CTC I, CTC II, and CTC III are phased with respect to each other, by operating valves V1, V2, V3 and V4 in proper sequence, so that a continuously phased system of analysis is achieved.

FIGS. 2a and 2b are identical to FIGS. 1a and 1b, respectively. Thus, it will also be observed that the series circuit of FIG. 2 can be operated in like fashion with the parallel circuit shown in FIG. 1.

The sequencing of the valves may be controlled by a programmed computer to automate the system. Of course, other controls can be employed.

The sample cell 16, reference cell 11, and analyzer 20 are shown schematically as separate units, but are, in fact, packaged as a single unit. Such units are made by Beckman (Model 1R-215B) for example, and use infrared detection to distinguish the various differences in carbon dioxide levels between the cells 11 and 16.

Having thus described the invention, what is sought to be covered by Letters Patent is presented by the appended claims.

What is claimed is:

1. A system for detecting the infestation of live insect within a commodity sample comprising:
   means for storing a fluid having a reference level of carbon dioxide;
   at least one commodity chamber for containing a commodity sample to be tested for infestation by live insects, said live insects generating carbon dioxide to be analyzed;
   a sample cell associated with said commodity chamber for receiving any generated carbon dioxide from said commodity chamber;
   a reference cell associated with said sample cell for establishing a background level of carbon dioxide in said system;
   first means for controlling the passage of a portion of said fluid containing said reference level of carbon dioxide from said storing means into said reference cell for establishing said background level of carbon dioxide in said reference cell;
   second means defining a closed loop comprising said storing means, said commodity chamber and said sample cell, means for circulating a portion of said fluid containing said reference level of carbon dioxide along said closed loop, so as to transfer any carbon dioxide generated in said commodity chamber to said sample cell; and
   means for measuring the total carbon dioxide level in said sample cell in respect of the carbon dioxide level in said reference cell, whereby the presence of live insects in said commodity sample is detected.

2. The system of claim 1, wherein said means for storing a fluid is a container for holding a given quantity of ambient air.

3. The system of claim 1, wherein said first and second means each comprises metering means for supplying said fluid at substantially equal rates through said sample cell and said reference cell.

4. The system of claim 1, further including pump means for passing said fluid along said first and second means.

5. The system of claim 4, wherein said pump means comprises a vacuum pump.

6. The system of claim 1, wherein said first and second means comprises means for defining a closed loop between said fluid storing means and said sample cell and said reference cell so as to seal the system and supply said sample cell and said reference cell with a reference level of carbon dioxide.

7. The system of claim 6, further comprising means for introducing said reference level of carbon dioxide into said closed-loop means, to calibrate the system.

8. The system of claim 6, wherein said closed-loop means comprises means for connecting said reference cell in parallel arrangement with respect to said commodity chamber and said sample cell.

9. The system of claim 6, wherein said closed-loop means comprises means for connecting said reference cell in series arrangement with respect to said commodity chamber and said sample cell.

10. The system of claim 7, further comprising a plurality of commodity chambers and valving means for selectively connecting said plurality of commodity chambers in fluid communication with said closed-loop means to provide a phased analyzing system.

11. A method of detecting the infestation of live insects within a commodity sample, comprising the steps of:
   (a) storing a given quantity of fluid containing a reference level of carbon dioxide;
   (b) circulating a portion of said stored fluid through a reference cell in a controlled manner to establish a controlled level of carbon dioxide in said reference cell;
   (c) incubating a commodity sample disposed within a commodity chamber to generate a sample level of carbon dioxide;
   (d) circulating a portion of said stored fluid in a controlled manner through said commodity chamber and said sample cell and then to said commodity chamber, in closed-loop fashion, so as to transfer any carbon dioxide generated in said commodity chamber to said sample cell; and (e) measuring any difference between carbon dioxide levels in said sample cell and said reference cell, respectively, to detect the presence of any living insects in the commodity sample.

12. The method of claim 11, further comprising the step of:

flushing said commodity chamber prior to step (c).

13. The method of claim 11, further comprising the step of:

prior to the incubating step (c), sealing said commodity chamber and said sample cell and said reference cell to define a closed loop.

14. The method of claim 13, further comprising the step of:

calibrating the system by introducing a given quantity of carbon dioxide to said closed loop.

* * * * *